US012788285B2

(12) United States Patent
Kim

(10) Patent No.: US 12,788,285 B2
(45) Date of Patent: *Nov. 10, 2026

(54) PORTABLE APPARATUS FOR NONINVASIVELY MEASURING BLOOD GLUCOSE LEVEL AND OPERATING METHOD THEREOF

(71) Applicant: TMRW Electronics, SARL, Luxembourg (LU)

(72) Inventor: Hoon Kim, Singapore (SG)

( * ) Notice: Subject to any disclaimer, the term of this patent is extended or adjusted under 35 U.S.C. 154(b) by 452 days.

This patent is subject to a terminal disclaimer.

(21) Appl. No.: 18/368,559

(22) Filed: Sep. 14, 2023

(65) Prior Publication Data

US 2024/0041360 A1 Feb. 8, 2024

Related U.S. Application Data

(63) Continuation of application No. 16/780,552, filed on Feb. 3, 2020, now Pat. No. 11,766,197, which is a (Continued)

(51) Int. Cl.

*A61B 5/1455* (2006.01)
*A61B 5/00* (2006.01)

(Continued)

(52) U.S. Cl.

CPC ........ *A61B 5/1455* (2013.01); *A61B 5/14532* (2013.01); *A61B 5/681* (2013.01);

(Continued)

(58) Field of Classification Search

CPC ... A61B 5/1455; A61B 5/14532; A61B 5/681; A61B 5/7278; A61B 5/0059;

(Continued)

(56) References Cited

U.S. PATENT DOCUMENTS 6,172,743 B1 1/2001 Kley .................. A61B 5/14532 356/39
2009/0270701 A1 10/2009 Osaki ................. A61B 5/14532 600/316
2017/0164878 A1 6/2017 Connor .................. G09B 19/00

FOREIGN PATENT DOCUMENTS

CA 2146856 C * 4/2004 ........... A61B 5/7239
CA 2674513 A1 8/2008 ........... A61B 5/1451

(Continued)

OTHER PUBLICATIONS

U.S. Appl. No. 16/780,552, filed Feb. 3, 2020.
U.S. Appl. No. 15/430,521, filed Feb. 17, 2017, U.S. Pat. No. 10,555,693.

*Primary Examiner* — Sean P Dougherty
(74) *Attorney, Agent, or Firm* — Bryan Cave Leighton Paisner LLP

(57) ABSTRACT

Disclosed in an embodiment is an operating method of portable apparatus for noninvasively measuring blood glucose levels. The method includes: (a) measuring a first signal value according to ambient environmental light when an LED for measuring signals which emits light with wavelengths to be absorbed into or scattered by glucose is switched off; (b) measuring a second signal value according to light which is scattered by or transmitted through subject tissue and enters a photodetecting unit when the LED for measuring signals is switched on; (c) calculating a glucose concentration measurement of a subject by using the first signal value and the second signal value; and (d) adjusting the quantity of the light radiated from the LED for measuring signals by feeding the difference between the glucose concentration measurement and a pre-established first reference value back to the driving current for the LED for measuring signals.

20 Claims, 9 Drawing Sheets

Related U.S. Application Data continuation of application No. 15/430,521, filed on Feb. 12, 2017, now Pat. No. 10,555,693.

(51) Int. Cl.

| | |
|---|---|
| ***A61B 5/01*** | (2006.01) |
| ***A61B 5/103*** | (2006.01) |
| ***A61B 5/145*** | (2006.01) |
| ***A61B 5/1486*** | (2006.01) |
| ***G01N 21/359*** | (2014.01) |

(52) U.S. Cl.

CPC .......... *A61B 5/7278* (2013.01); *A61B 5/0059* (2013.01); *A61B 5/0071* (2013.01); *A61B 5/0075* (2013.01); *A61B 5/0088* (2013.01); *A61B 5/01* (2013.01); *A61B 5/1032* (2013.01); *A61B 5/1451* (2013.01); *A61B 5/1486* (2013.01); *A61B 5/7203* (2013.01); *A61B 5/7228* (2013.01); *A61B 2560/0223* (2013.01); *A61B 2560/0252* (2013.01); *A61B 2562/0233* (2013.01); *G01N 21/359* (2013.01)

(58) Field of Classification Search

CPC ... A61B 5/0071; A61B 5/0075; A61B 5/0088; A61B 5/01; A61B 5/1032; A61B 5/1451; A61B 5/1486; A61B 5/7203; A61B 5/7228; A61B 2560/0223; A61B 2560/0252; A61B 2562/0233; G01N 21/359

See application file for complete search history.

(56) References Cited

FOREIGN PATENT DOCUMENTS

| | | | | | |
|---|---|---|---|---|---|
| CA | 2686065 | A1 | | 11/2008 | ......... A61B 5/14532 |
| EP | 3228244 | A1 | * | 10/2017 | ......... A61B 5/14532 |

* cited by examiner

PORTABLE APPARATUS FOR NONINVASIVELY MEASURING BLOOD GLUCOSE LEVEL AND OPERATING METHOD THEREOF

CROSS-REFERENCE TO RELATED APPLICATIONS

This application is a continuation application of U.S. patent application Ser. No. 16/780,552 filed on Feb. 3, 2020, which is a continuation of U.S. patent application Ser. No. 15/430,521 filed on Feb. 12, 2017 (now U.S. Pat. No. 10,555,693 issued on Feb. 11, 2020), the contents of which are all hereby incorporated by reference herein in their entirety.

TECHNICAL FIELD

The present disclosure relates to an apparatus for noninvasively measuring blood glucose levels and more particularly to an portable apparatus for noninvasively measuring blood glucose levels which is conveniently carried, capable of being worn on a human body and capable of exactly measuring blood glucose levels and an operating method thereof.

RELATED ART

It is necessary for those who are sensitive to a change in blood glucose levels such as patients with diabetes to monitor the blood glucose level that undergoes sharp changes in their daily life including exercise, meals and others. Therefore, there is a tendency for conventional apparatuses for invasively measuring blood glucose levels to become smaller in terms of size. However, such apparatuses go with hygiene and safety issues in that it is required that blood should be drawn for using them and moreover, it is difficult to measure the level in a continuous mode.

Recently, research and development are performed regarding apparatuses for measuring blood glucose levels in a noninvasive mode while such apparatuses using light are gaining special interest.

A typical apparatus for noninvasively measuring blood glucose levels, which uses light, generally makes use mainly of near infrared rays the wavelength, of which ranges from 1,100 to 1,600 nm, which are absorbed in the covalent bonds of C—H, O—H and others of glucose. Because almost all of the rays which range roughly from 1,100 to 1,600 nm in terms of wavelength are absorbed into other biogenic substances, for example water ($H_2O$), as illustrated in FIG. 1, light the intensity of which is over a certain value is necessary or various techniques are further required such as polarized spectroscopy in order to separate related components from each other. Moreover, light sources such as white halogen tungsten lamps or laser diodes (LDs), which are not easy to miniaturize or lower power consumption, are required for this range of wavelengths while it is not easy, based on existing technology, to use light sources such as light emitting diodes (LEDs), which are easy to miniaturize and lower power consumption.

A typical silicon photodiode (PD) detector (hereinafter referred to also as "photodetecting unit") detects mainly those rays, which range from 400 to 1,100 nm in terms of wavelength, not the rays the wavelength of which ranges from 1,100 to 1,600 nm as introduced above. Among these light sources, those which range from 800 to 900 nm have the largest depth of penetration. This range of wavelengths is called optical window because less light is absorbed into water and being interrupted with other substances such as hemoglobin in this range.

When such a silicon PD is employed as a detector for achieving the apparatus for noninvasively measuring blood glucose levels, the apparatus can be miniaturized because it is possible to make use of wavelengths which range from 400 to 1,100 nm. However, because a sufficiently high value of SN (signal to noise) ratio is required to measure glucose contained in blood in small quantities (about 0.01%) by employing the silicon PD as a detector, a high-sensitivity photodetector should be used. Meanwhile, because the maximum electrostatic capacity of a PD which detects light is in proportion to the light receiving area, such a PD employed as a detector should have a considerably large light receiving area so as to detect the response signals of the trace of glucose in blood. As a result, it is not easy to realize the portable apparatus for noninvasively measuring blood glucose that falls within the tolerance (i.e. 10 mg/dL or below) which is inevitably required for such an apparatus to come into common use, by sufficiently enlarging the light receiving area of the silicon PD used for portable or wearable devices.

In this regard, in order to solve the problems of the existing technology and fit into portable devices, technology to miniaturize and lower the power consumption of the apparatus for noninvasively measuring blood glucose by using typical LEDs as the light source, which emit light having wavelength in range of 400 to 1,000 nm instead of white halogen tungsten lamps or LDs, is increasingly demanded.

The above information disclosed in this Background section is only for enhancement of understanding of the background of the disclosure and it may therefore contain information that does not form the prior art that is already known to a person of ordinary skill in the art.

SUMMARY

In order to solve these problems of the existing technology, the present disclosure provides the apparatus for noninvasively measuring blood glucose levels which is capable of accurately measuring the glucose levels in blood even by using LEDs, which are capable of being miniaturized and lowering power consumption, instead of white halogen tungsten lamps or LDs, which are not easily miniaturized and do not easily lower power consumption.

In addition, the present disclosure provides the apparatus for noninvasively measuring blood glucose levels, which ensures accurate measuring results irrespective of the influence of external environment such as ambient quantity of light and temperature and the biometric characteristics inherent to a user who wears the apparatus such as skin color and skin tissue.

The operating method of the portable apparatus for noninvasively measuring blood glucose levels according to a first aspect of the present disclosure includes:

(a) measuring a first signal value according to ambient environmental light and temperature by using a light measuring unit in the situation where an LED for measuring signals which emits light with wavelengths to be absorbed into or scattered by glucose is switched off;

(b) measuring a second signal value according to light which is scattered by or transmitted through subject tissue and enters the light measuring unit in the situation where the LED for measuring signals is switched on;

(c) calculating a glucose concentration measurement of a subject by using the first signal value and the second signal value; and (d) adjusting the quantity of the light radiated from the LED for measuring signals by feeding the difference between the glucose concentration measurement and a pre-established first reference value back to driving current for the LED for measuring signals.

The portable apparatus for noninvasively measuring blood glucose levels according to another aspect of the present disclosure includes:

the LED for measuring signals which emits light with wavelengths absorbed into or scattered by glucose;

the photodetecting unit which includes at least one light receiving element and converts the light received by the light receiving element to an electrical signal; and a control unit which is connected to the photodetecting unit to collect the first signal value detected according to ambient environmental light and temperature in the situation where the LED for measuring signals is switched off and the second signal value detected according to light, which is scattered by or transmitted through subject tissue, and enters the photodetecting unit in the situation where the LED for measuring signals is switched on, calculate the glucose concentration measurement of the subject by using the first signal value and the second signal value, and adjust the quantity of the light radiated from the LED for measuring signals by feeding the difference between the glucose concentration measurement and the pre-established first reference value back to the driving current for the LED for measuring signals.

In addition, another aspect of the present disclosure provides a computer readable recording medium on which a program for achieving the operating method according to the first aspect is recorded.

According to an embodiment of the present disclosure, it is possible to measure reliable blood glucose levels irrespective of the influence of ambient environmental light and temperature or the differences in subject tissue structures and skin colors.

In addition, according to some embodiment of the present disclosure, it is possible to achieve the portable apparatus for measuring blood glucose levels which is capable of measuring sufficiently reliable blood glucose levels and being miniaturized enough to be worn on a human body even when the typical LED is used as the light source.

BRIEF DESCRIPTION OF THE DRAWINGS

The above and other features and advantages of the present disclosure will be more clearly understood from the following detailed description taken in conjunction with the accompanying drawing, in which.

DETAILED DESCRIPTION

Figure 1:
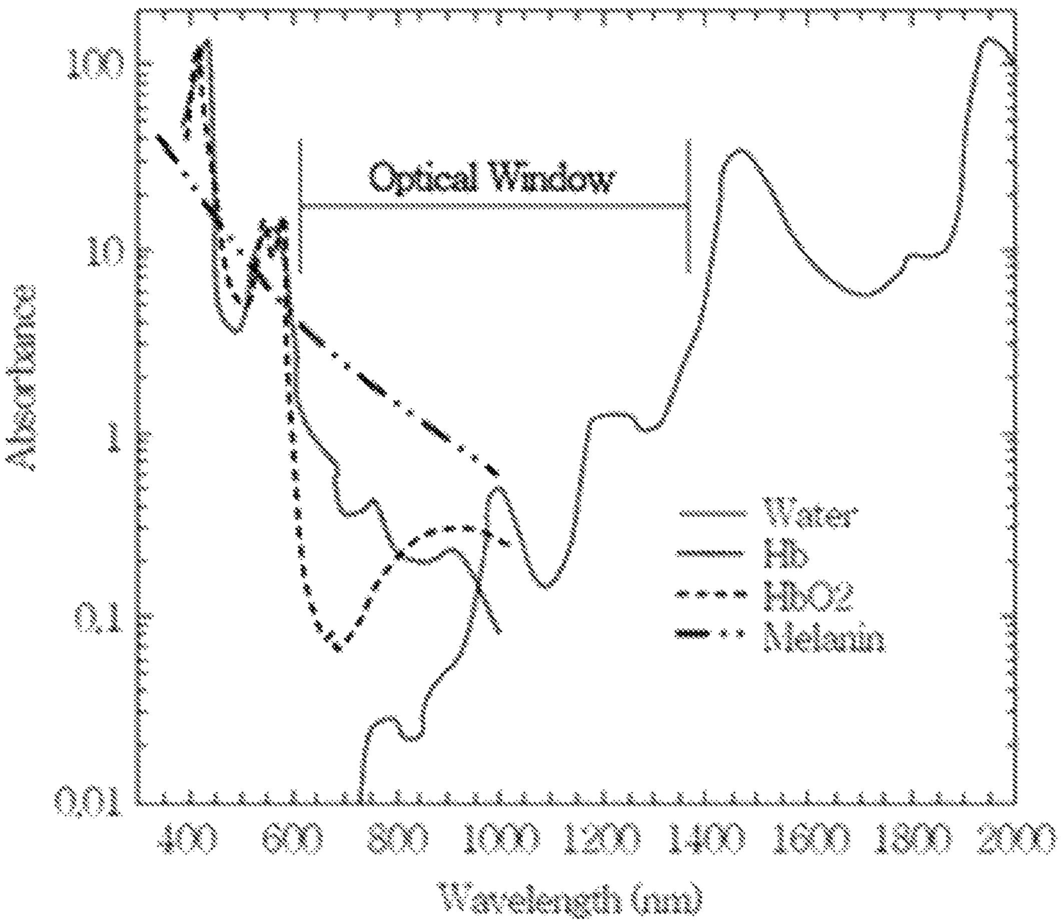
FIG. 1 is a graph, which shows light absorbance in terms of wavelength in biogenic substances.

Although the present disclosure can be embodied in many different forms, only a few specific embodiments are exemplified in the accompanying drawing, which will be described in detail below. However, the present disclosure should not be limited to the specific embodiments and should be construed as including all conversions, equivalents and replacements included in the thoughts and technical scope disclosed. When it is determined that detailed description on related known technology for describing the embodiments, such detailed description will be omitted.

Terms such as a first, a second and the like may be used for describing various technical features, which should not be limited to such terms. Such terms are used only for the purpose of distinguishing a feature from another one.

Terms in the present application are used only for describing the specific embodiments and are not used with the intention of limiting the scope of patent rights. A singular form includes its plural form unless the context otherwise requires explicitly different meaning. Terms such as 'include', 'have' and the like in the present application specify that there exists the feature, figure, step, action, component, part or combination of them stipulated in the present specification and should not be construed as excluding in advance the existence or the possible addition of one or more other features, figures, steps, actions, components, parts or combination of them.

The present disclosure will be described more fully hereinafter with reference to the accompanying examples, where same or corresponding features are given an identical reference character and related description that would otherwise be duplicated will be omitted.

Figure 2A:
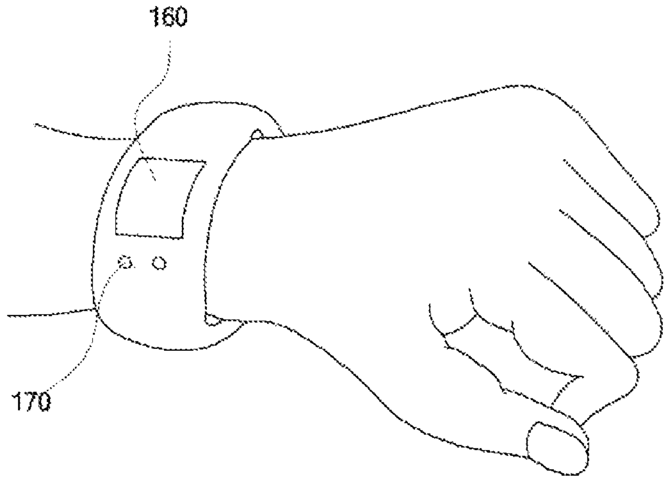
FIGS. 2A and 2B are conceptual diagrams, which illustrate the components of the portable apparatus for noninvasively measuring blood glucose levels according to an embodiment of the present disclosure.
Figure 2B:
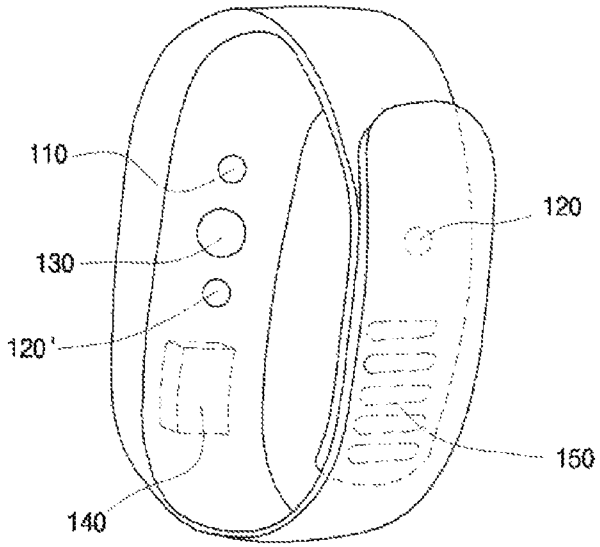

FIGS. 2A and 2B are conceptual diagrams, which illustrate the components of the portable apparatus for noninvasively measuring blood glucose levels according to an embodiment of the present disclosure.

Referring to FIGS. 2A and 2B, the portable apparatus for noninvasively measuring blood glucose levels 100 (hereinafter the 'blood glucose level measuring apparatus for convenience) could be realized in the form of a wearable device, which is worn on a human body part, such as a watch or smart band to be worn on the wrist, a smart ring worn on the finger and the like. Hereinafter, an example realized in the form of a wearable watch will be described.

The blood glucose level measuring apparatus 100 includes a first LED 110, the second LED and the photodetecting unit 130, which are arranged on its inner surface, which faces the wrist of a wearer and could include, on its outer surface, a display unit 160 and a user interface 170. In addition, the blood glucose level measuring apparatus has the control unit 140 inside the blood glucose level measuring apparatus and could further include a fastening mechanism 150 so that the blood glucose level measuring apparatus is worn on the wrist.

The first LED 110 is a light source to use as the reference for temperature correction and measured signals and radiates light having wavelength range of 600 to 800 nm, which is neither absorbed in nor scattered by glucose.

The second LED 120 is a light source for measuring signals and radiates light having wavelength range of 800 to 1,000 nm, which is absorbed in or scattered by glucose, the object to measure by means of the blood glucose level measuring apparatus 100.

The photodetecting unit 130 detects the intensity of the light radiated from the first LED 110 and the second LED 120, and transmitted through or reflected off bodily tissue. It is desirable to realize the photodetecting unit 130 by using the tunnel junction light receiving element, which requires a smaller light receiving area, so that the blood glucose level measuring apparatus according to the present disclosure is easily miniaturized. The tunnel junction light receiving element could be selected from the high-sensitivity light receiving elements disclosed in U.S. Pat. No. 8,569,806, Unit pixel of image sensor and photo detector thereof, U.S. Pat. No. 8,610,234 and others. The tunnel junction light receiving element has a structure in which a thin dielectric film joined between two conductors or semiconductors and refers to an element, which operates based on the tunneling effect that occurs in such a dielectric film.

The tunnel junction light receiving element controls the current in an internal channel of the photodetecting unit 130 because a change in the quantity of electric charges of a light receiving unit acts as the field effect, whereas a typical photodiode distinguishes brightness based only on the quantity of electric charges accumulated in the capacity. In addition, a signal could be amplified within the tunnel junction light receiving element itself. Therefore, the photodetecting unit 130 is capable of generating a photocurrent flow that is several hundred times of that of an existing photodiode at an identical quantity of light by using the tunnel junction light receiving element. Consequently, the photodetecting unit 130 could be miniaturized irrespective of the entire size of the blood glucose level measuring apparatus 100. The photodetecting unit 130 employing the tunnel junction light receiving element will be described in detail below with reference to FIG. 5.

The first LED 110 and the photodetecting unit 130 are arranged on the same surface so that both of them face an identical surface of the subject. In this case, the photodetecting unit 130 converts the reflected rays of the light radiated from the first LED 110 into electrical signals, wherein the reflected light that enters the photodetecting unit 130 shows a measurement irrelevant to glucose concentrations because the light radiated from the first LED 110 has wavelengths which range from 600 to 800 nm, which are neither absorbed in nor scattered by glucose. The blood glucose level measuring apparatus 100 of the present disclosure is driven in various operating modes, where the first LED 110 might be used, or not, during measurement depending on the selected operating mode.

Figure 3A:
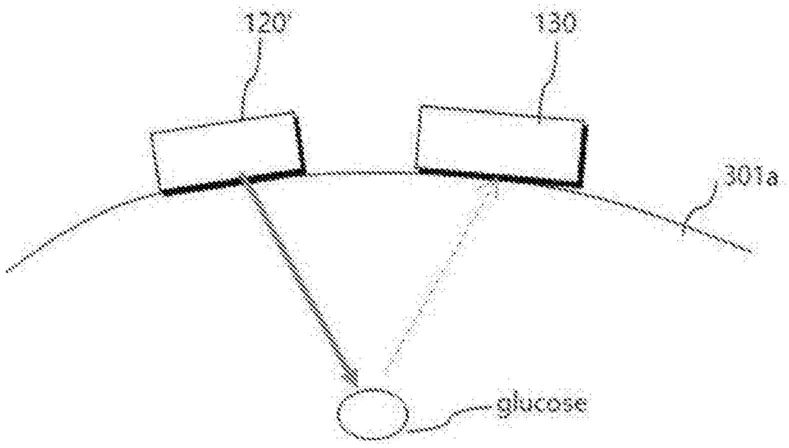
FIGS. 3A and 3B are diagrams, which describe the arrangement and operation of the LED for measuring signals (a second LED) according to a driving mode of the portable apparatus for noninvasively measuring blood glucose levels according to an embodiment of the present disclosure.
Figure 3B:
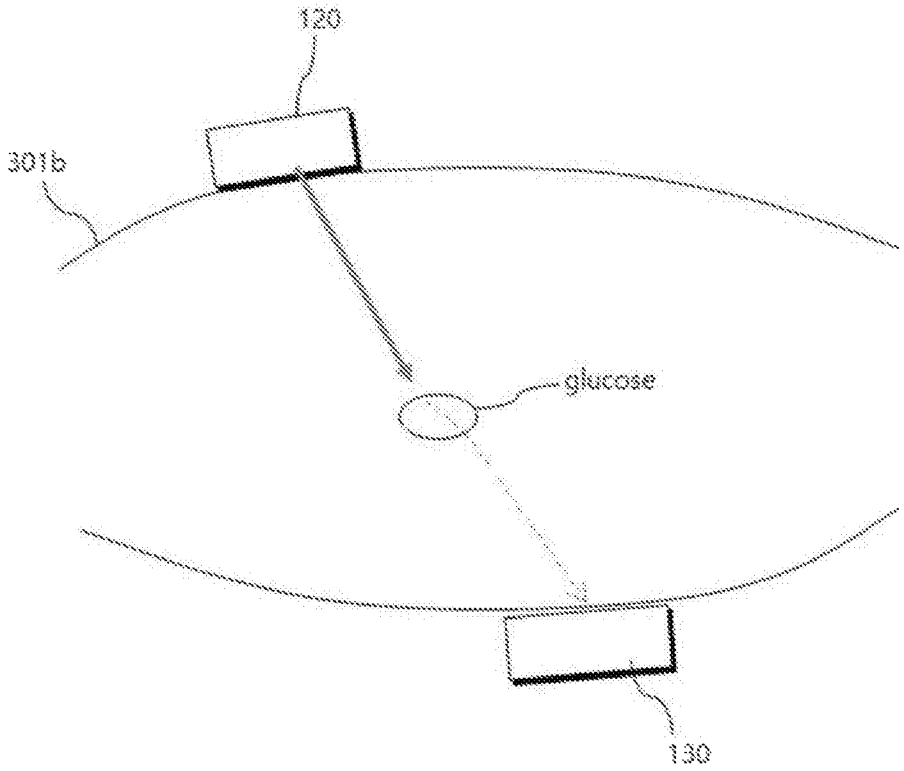

The second LED 120 can be arranged on the same surface as the photodetecting unit 130 or on the other surface opposite to the photodetecting unit 130 with the subject in between. Referring to FIGS. 3A and 3B, arranging the second LED 120 on the same surface as the photodetecting unit 130 as illustrated in FIG. 3A refers to a state where the blood glucose level measuring apparatus 100 is formed in the reflective mode, wherein both the second LED 120 and the photodetecting unit 130 face an identical surface of the subject and the photodetecting unit 130 converts the light radiated from the second LED 120 and then reflected off the subject 301*a* into electrical signals.

Meanwhile, when the second LED 120 is arranged on the other surface opposite to the photodetecting unit 130 as illustrated in FIG. 3B, which means the blood glucose level measuring apparatus 100 is formed in the transmission mode, the second LED 120 faces the photodetecting unit 130 with the subject 301*b* in between and the photodetecting unit 130 converts the light radiated from the second LED 120 and then transmitted through the subject 301*b* into electrical signals.

Referring to FIGS. 2A and 2B again, the second LED 120 is used as the light source for measuring signals and radiates light having wavelength range of 800 to 1,000 nm, which are absorbed in or scattered by glucose. Therefore, the quantity of the light radiated from the second LED 120 and then scattered by, as in the reflective mode or transmitted through, as in the transmission mode, glucose and enters the photodetecting unit 130 changes according to the glucose concentration of the subject.

The control unit 140 includes at least one component for controlling the first LED 110, the second LED 120 and the photodetecting unit 130. For example, the control unit 140 includes at least one core and could further include a digital signal processor (DSP), a microprocessing unit (MPU), a microcontroller unit (MCU) and the like.

The control unit 140 controls the first LED 110, the second LED 120 and the photodetecting unit 130 to measure the quantity of the light scattered by, as in the reflective mode, or transmitted through, as in the transmission mode, the glucose in the subject, quantifies the glucose concentration based on the measured quantity of the light and measures the blood glucose level in the body of the subject based on the quantified glucose concentration.

Measurements of the blood glucose level measuring apparatus 100 can vary depending on external factors such as ambient environmental light, temperature and others because the blood glucose level measuring apparatus 100 is portable. In addition to these external factors including ambient environmental light, the biometric characteristics inherent to the subject such as skin color, body temperature, tissue composition and others could affect the change in the measurements. Therefore, the control unit 140 quantifies the measured glucose concentration independently of such external environment and the subject themselves by correcting the displacement of the measurements due to the environmental factors or the biometric characteristic inherent to the subject to ensure an identical measuring result for an identical blood glucose level.

Figure 4:
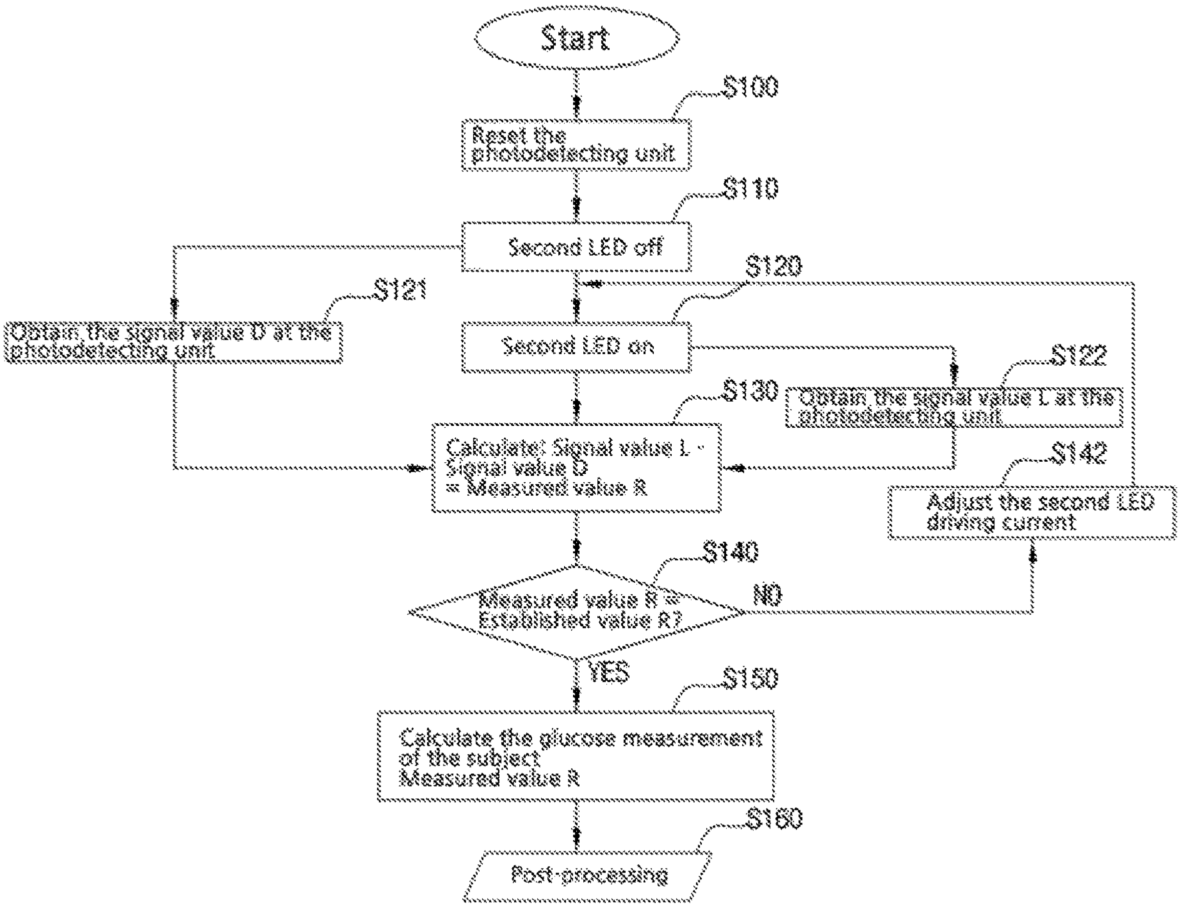
FIG. 4 is a flowchart, which describes a method of measuring blood glucose levels by correcting environmental light for the portable apparatus for noninvasively measuring blood glucose levels according to an embodiment of the present disclosure.

FIG. 4 describes the process for correcting the error of measurements due to environmental light in the blood glucose level measuring apparatus 100. The present disclosure will be described hereinafter on the presumption that the blood glucose level measuring apparatus 100 is formed in the reflective mode.

Referring to FIG. 4, the blood glucose level measuring apparatus 100 measures blood glucose and body composition by using the second LED 120 as the light source for measuring signals. As a step prior to measuring, the control unit 140 resets the photodetecting unit 130 when the second LED is switched off.

After that, the photodetecting unit 130 is driven in the situation where the second LED 120 is switched off and a signal value detected due to the ambient environment, a signal value D, is measured S121. Effects of ambient environmental light and ambient temperature, with the effects of glucose excluded, are incorporated into the signal value D because the signal value D is measured when the second LED 120, which emits light to be absorbed in glucose, is not driven.

After that, in the situation where the second LED 120 is switched on in order to radiate light onto the subject S120, the photodetecting unit 130 is driven and a signal value due to the light which is radiated from the second LED 120 and scattered by or reflected off the subject tissue and enters the photodetecting unit, a signal value L, is measured S122. The signal value L is influenced by the quantity of the light having wavelength range of 800 to 1,000 nm, radiated from the second LED 120 when the second LED 120 is switched on and then absorbed in and scattered by the glucose in the subject. Moreover, the signal value L has a peak value higher than that of the signal value D, which is influenced only by ambient environmental light and biogenic substances other than glucose, because the signal value L is obtained by using the second LED 120 as the light source.

After that, the control unit 140 calculates a measured value R based on the obtained signal value D and the signal value L S130. The measured value R is an offset produced by correction when the signal value D is subtracted from the signal value L. The control unit 140 produces the results from measuring the blood glucose level of the subject by matching the measured value R with a blood glucose level table established to be corresponding to each glucose concentration. The blood glucose level table is stored in the blood glucose level measuring apparatus.

After that, the control unit 140 compares the produced measured value R with a reference value established in connection with the blood glucose level table, an established value R S140. When the result from subtracting the established value R from the measured value R is positive, the control unit 140 reduces the quantity of the radiated light by reducing the driving current for the second LED 120. On the contrary, when the result from subtracting the established value R from the measured value R is negative, the control unit 140 increases the quantity of the radiated light by increasing the driving current for the second LED 120 S142. The second LED radiates an adjusted value of the quantity of light based on the value of the driving current fed back from the previous step, thereby correcting the quantity of light to a constant value at all times and making the corrected quantity of light incident on the subject independently of ambient environmental light. This step could be repeated multiple times until the measured value R becomes equal to the established value R, wherein the state where the measured value R and the established value R are equal to each other includes the state where the difference in both values falls within a tolerance. The established value R could be a value experimentally obtained.

When the measured value R measured in the previous step is equal to the established value R, the control unit 140 matches the measured value R with the blood glucose level table and selects the corresponding blood glucose level. The selected blood glucose level could be a value experimentally quantified and the blood glucose level of the subject could be calculated based on the selected blood glucose level S150. For example, each value which constitutes the blood glucose level table could be a value produced based on the results obtained simultaneously via an invasive blood glucose level measuring apparatus and the noninvasive blood glucose level measuring apparatus according to the present disclosure.

Via the steps, the blood glucose level measuring apparatus 100 obtains constant measuring results by correcting the measurement error due to ambient environmental light and ambient temperature save for the light source directly radiated onto the subject for measuring the signals.

Meanwhile, the high-sensitivity detector should be used for the photodetecting unit in order to detect a minute change in the glucose inside the subject. The tunnel junction light receiving element is used in the present disclosure as an example of the high-sensitivity detector.

Figure 5:
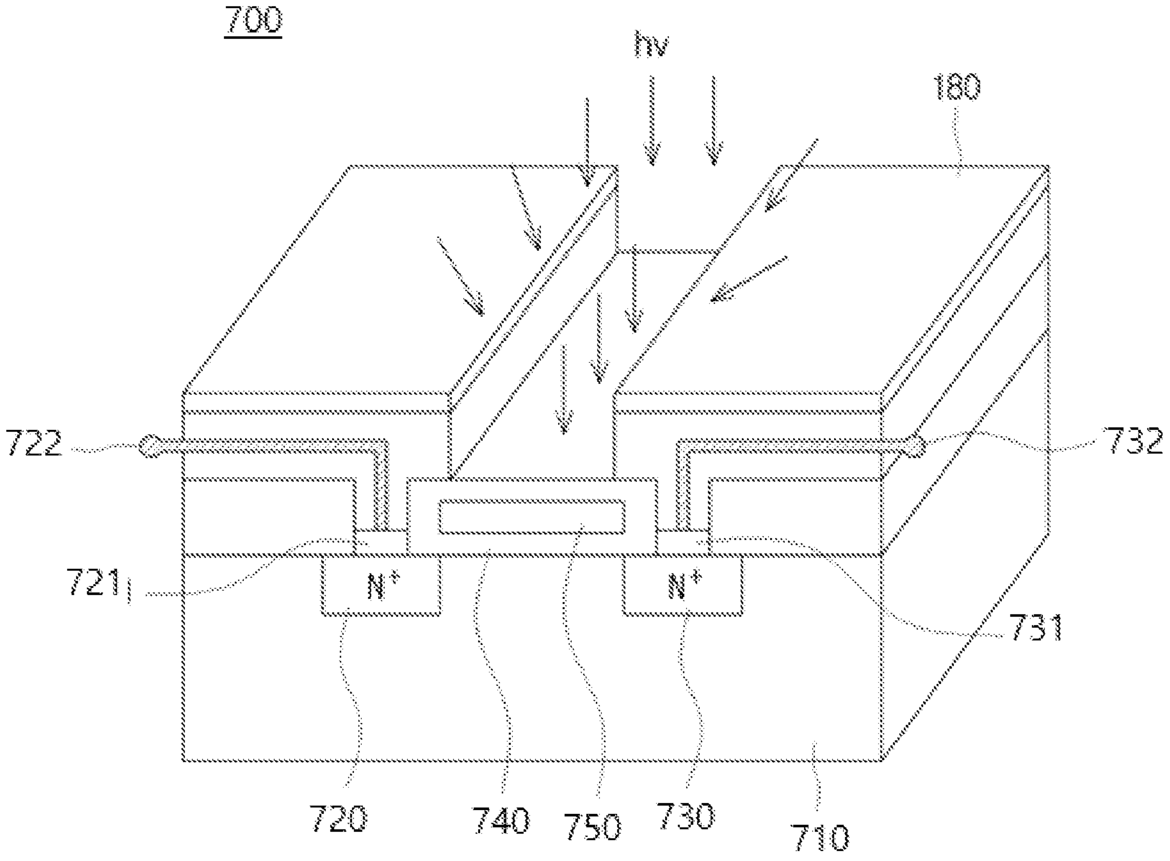
FIG. 5 is a diagram, which shows an example of the structure of a tunnel junction light receiving element used as the detector of the portable apparatus for noninvasively measuring blood glucose levels according to an embodiment of the present disclosure.

FIG. 5 illustrates an example of the tunnel junction light receiving element to achieve the photodetecting unit 130 according to an embodiment of the present disclosure.

The tunnel junction light receiving element has a structure in which the thin dielectric film joined between two conductors or semiconductors and refers to an element, which operates based on the tunneling effect that occurs in such a dielectric film.

The tunnel junction light receiving element 700 could have n-MOSFET structure as an example, wherein the tunnel junction light receiving element 700 is formed on a P-type substrate 710 and includes an N+ diffusion layer 720 and another N+ diffusion layer 730, which corresponds the source and the drain, respectively, of a typical NMOS electronic element. The N+ diffusion layers 720, 730 will be referred to as the "source" and the "drain", respectively, of the tunnel junction light receiving element 700 hereinafter.

Metallic contacts 721, 731 are formed on the source 720 and the drain 730 and each of the metallic contacts 721, 731 is connected to the exterior via each of metallic lines 722, 732.

The thin dielectric film 740 is formed between the source 720 and the drain 730 while polysilicon 750, which corresponds to the gate of a typical NMOS structure is formed above the dielectric film 740, wherein P-type impurities are doped in the polysilicon 750. The polysilicon 750 acts as the light receiving unit for receiving light in the tunnel junction light receiving element 700. The polysilicon 750 will be referred to as the "light receiving unit".

The light receiving unit 750 are separated from the source 720 and the drain 730 with the dielectric film 740. The tunneling effect occurs between the light receiving unit 750 and the source 720 or the drain 730, wherein it is desirable for the dielectric film 740 to have a thickness of 10 nm or less for promoting the tunneling effect.

When light having its energy higher than the binding energy of the impurities doped above the light receiving unit 750 and the band gap of the polysilicon is radiated, electron-hole pairs are generated due to light excitation in the light receiving unit 750 and the electrons and the holes, which constitute the generated electron-hole pairs, exist in the state of electrons and holes, respectively, for a specific period until they are recombined. The separated electrons move freely outside the grain boundary of the light receiving unit 750. At this time, when voltage is applied to the source 720 or the drain 730, the electrons are accumulated near the boundary of the light receiving unit 750 adjacent to the source or the drain, which generates a specific amount of electric field between the source 720 and the drain 730 and the light receiving unit 750.

As the strength of the generated electric field increases, the tunneling occurs more easily near the boundary between the source 720 and the drain 730 and the light receiving unit 750. At the instant certain energy level conditions are met near the boundary, the tunneling of the accumulated electrons occurs, and by this phenomenon, the electrons accumulated near the boundary of the light receiving unit 750 tunnel the dielectric film 740 to transfer to the source 720 or the drain 730. This is equivalent to an increase of the number of holes, or the quantity of positive charges, as many as the number of the electron lost, which lowers the channel threshold voltage, thereby causing a current flow via the channel.

The light receiving element with this structure is capable of generating a photocurrent flow that is more than several hundred up to thousand times of that of an existing photodiode at an identical quantity of light. A typical photodiode distinguishes brightness based only on the quantity of electric charges accumulated in the capacity. On the contrary, the tunnel junction light receiving element 700 generates a large current flow in the channel because a minute change in the quantity of electric charges of a light receiving unit 750 due to light acts as a large amount of the field effect. In addition, electric charge is supplied infinitely via the drain when necessary, which provides an effect of amplifying the signal within the light receiving element itself. Therefore, because an independent signal amplifying element is not required and because this technology could be achieved in a small area, it is possible to realize the blood glucose level measuring apparatus according to the present disclosure in the form of the small wearable device such as wearable watches and rings by forming the photodetecting unit by using the tunnel junction light receiving element. Having said that, another kind of the light receiving element having functions and performance equivalent or corresponding to those of the tunnel junction light receiving element could be used for forming the light measuring unit even when the tunnel junction light receiving element is not employed for forming the light measuring unit of the blood glucose level measuring apparatus 100 according to the present disclosure.

Figure 6:
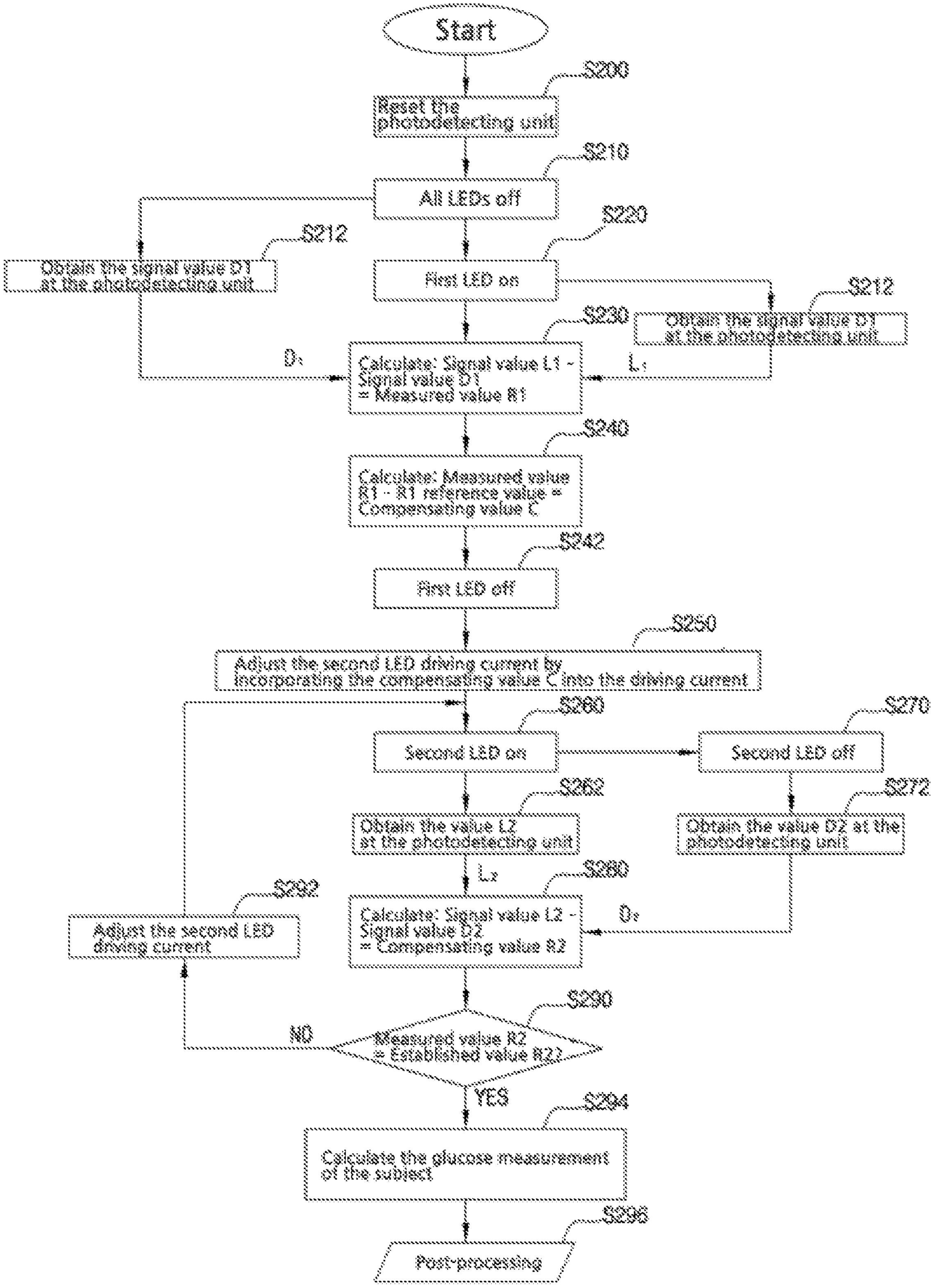
FIG. 6 is a flowchart, which describes a method of measuring blood glucose levels by correcting wearer environmental conditions including body temperature, skin color and the like in the portable apparatus for noninvasively measuring blood glucose levels according to an embodiment of the present disclosure.

FIG. 6 describes the process of correcting the measurement error caused by the body temperature and skin characteristics of the subject in the blood glucose level measuring apparatus 100.

In general, the signal value of the measured reflected light changes due to the body temperature and skin characteristics of the subject, wherein the skin characteristics include skin colors, skin composition, epidermis or dermis thickness and others. This is because light is scattered by or transmitted through glucose to a different degree depending on the changes in the skin characteristics or body temperature of the subject even when the amount of the glucose in the subject remains the same. Therefore, it is necessary to correct the measurement error according to the temperature or skin characteristics of the subject in the blood glucose level measuring apparatus 100.

Referring to FIG. 6, the blood glucose level measuring apparatus 100 measures glucose and body composition by using the first LED 110 as the reference light source for temperature correction and measured signals simultaneously with the second LED 120 as the reference light source for measuring signals. As step prior to measuring, the control unit 140 resets the photodetecting unit 130 in the situation where the first LED 110 and the second LED 120 are switched off S200.

After that, the photodetecting unit is driven in the situation where both of the first LED 110 and the second LED 120 are switched off and a signal value detected due to the ambient environment, a signal value D1, is measured S210, S212. Effects of ambient environmental light and ambient temperature, with the effects of glucose excluded, are incorporated into the signal value D1 because the signal value D1 is measured when the second LED 120 as the light source to emit light to be absorbed in or scattered by glucose is not driven.

After that, in the situation where the first LED 110 is switched on in order to radiate light onto the subject S220, the photodetecting unit 130 is driven and a signal value due to the light which is radiated from the first LED 110 and scattered by or reflected off the subject tissue and enters the photodetecting unit, a signal value L1, is measured S222. The signal value L1 is influenced by the quantity of the light having wavelength range of about 600 to 800 nm radiated from the first LED 110 when the first LED 110 is switched on and the second LED 120 is still switched off and then absorbed in and scattered by the tissue in the subject. The light, which is radiated from the first LED 110 and has a wavelength from 600 to 800 nm is absorbed in glucose to a considerably low extent. Therefore the effects only of substances such as cholesterol and alcohol, save for glucose, are incorporated into the measured signal value L1.

In addition, the measured signal value L1 contains the errors caused by the effects of the body temperature and skin characteristics of the subject because the scattering rate and the absorption rate of the light radiated from the first LED 110 change according to the body temperature or skin characteristics of the subject.

After that, the control unit 140 calculates a measured value R1 based on the obtained signal value D1 and the signal value L1 S230. The measured value R1 is produced by correction when the signal value D1 is subtracted from the signal value L1. The control unit 140 compares the measured value R1 with a R1 reference value, which is a pre-established value with reference to a standard subject, thereby calculating the difference between both values S240. The calculated difference becomes a compensating value C and the compensating value C is fed back to adjusting the intensity of the second LED 120 as the light source for measuring signals for driving the second LED 120 so that the quantity of light is adjusted properly according to the temperature change and skin characteristics of the subject.

Figure 7:
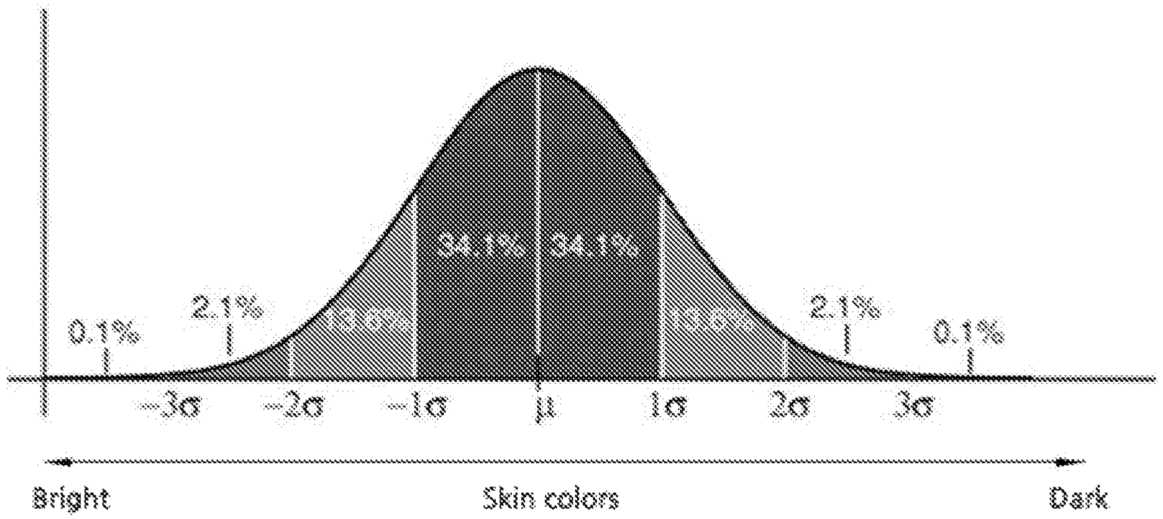
FIG. 7 is a graph, which exemplarily shows the rate of change in glucose detection according to skin colors.

A previously stored table of glucose detection changes according to skin colors could be referred to for calculating the compensating value C. FIG. 7 illustrates an exemplary graph with regard to this calculation method, wherein the graph classifies skin colors into multiple bins from the brightest one to the darkest one according to the Gaussian distribution. The control unit 140 selects a bin corresponding to the difference between the measured value R1 and the R1 reference value and is capable of selecting the value corresponding to the selected bin as the compensating value C to incorporate the compensating value C into adjusting the amount of the driving current for the second LED 120.

After that, the control unit 140 switches the first LED 110 off S242 and then resets the photodetecting unit 130.

After that, the control unit 140 adjusts the driving current for the second LED 120 based on the obtained compensating value C S250. The control unit 140 is capable of reducing the quantity of light radiated from the second LED 120 by reducing the driving current of the second LED 120 S250 when the compensating value C is positive. On the contrary, the control unit 140 is capable of increasing the quantity of light radiated from the second LED 120 by increasing the driving current of the second LED 120 when the compensating value C is negative. The compensating value C and the amount of the driving current change according to the compensating value C could be matched with each other with reference to a pre-established matching table.

After that, the control unit 140 switches the second LED 120 on so that the second LED 120 radiates the light, of which the quantity is adjusted into a value to which the compensating value C has been incorporated S260 and measures a signal value generated by the light which is radiated from the second LED 120 and scattered by or reflected off the subject tissue and then enters the photodetecting unit, a signal value L2, by using the photodetecting unit 130 S262. After that, a signal value D2 due to the reflected light is obtained by using the photodetecting unit 130 S272 in the situation where the second LED 120 is switched off S270. The control unit 140 calculates a measured value R2 based on the obtained signal value L2 and the obtained signal value D2 S280. The measured value R2 is produced by correction when the signal value D2 is subtracted from the signal value L2 and the control unit 140 calculates the blood glucose level measuring results of the subject by matching the measured value R2 with the blood glucose level table established to correspond to each glucose concentration S280, wherein the blood glucose level table could be identical to what is referred to in FIG. 4.

After that, the control unit 140 compares the produced measured value R2 with a reference value established in connection with the blood glucose level table, an established value R2 S290. When the result from subtracting the established value R2 from the measured value R2 is positive, the control unit 140 reduces the quantity of the radiated light by reducing the driving current for the second LED 120. On the contrary, the result from subtracting the established value R2 from the measured value R2 is negative, the control unit 140 increases the quantity of the radiated light by increasing the driving current for the second LED 120 S292. The second LED radiates an adjusted value of the quantity of light based on the value of the driving current fed back from the previous step, thereby correcting the quantity of light to a constant value at all times and making the corrected quantity of light incident on the subject independently of ambient environmental light. This step could be repeated multiple times until the measured value R2 becomes equal to the established value R2. The established value R2 could be a value experimentally obtained.

When the measured value R2 measured in the previous step is equal to the established value R2, the control unit 140 matches the measured value R2 with the blood glucose level table and selects the corresponding blood glucose level. The selected blood glucose level could be a value experimentally quantified and the blood glucose level of the subject could be calculated based on the selected blood glucose level S294.

Through the correction steps, the blood glucose level measuring apparatus 100 is capable of practically correcting the blood glucose levels by correcting the measurement error due to ambient environmental light and ambient temperature save for the light source directly radiated onto the subject for measuring the signals and by correcting the quantity of light by incorporating the error caused by the skin color, skin characteristics and body temperature at the moment of measuring inherent to the subject into the quantity of light, thereby obtaining constant measuring results independently of the conditions.

Figure 8A:
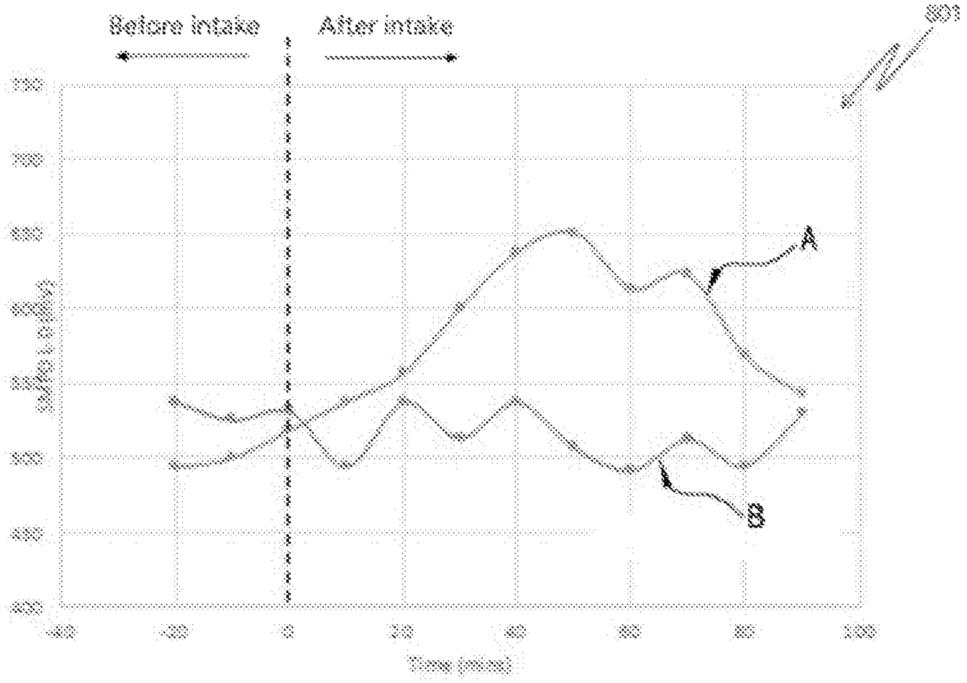
FIGS. 8A and 8B are graphs, which show the experimental results of the portable apparatus for noninvasively measuring blood glucose levels according to an embodiment of the present disclosure.
Figure 8B:
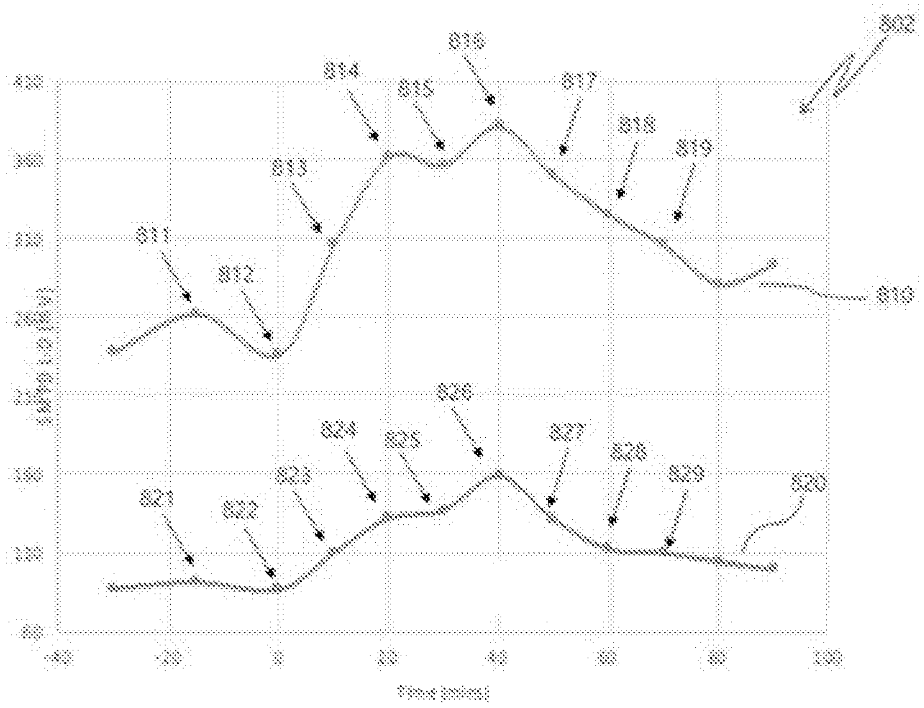

FIGS. 8A and 8B illustrate the experimental results of the blood glucose level measuring apparatus according to an embodiment of the present disclosure.

A graph 801 in FIG. 8A plots the measurement results of the blood glucose level apparatus 100 before and after the subject takes in water and grape juice, where the horizontal axis represents the passage of time while the vertical axis represents the difference, as measured with the photodetecting unit 130, between the signal value detected when the second LED 120 is switched off and the signal value after the second LED 120 radiates light when the second LED 120 is driven by the driving current adjusted according to the actions described above, or L-D.

Referring to the graph 801, the measurements of the blood glucose level measuring apparatus 100 rapidly increase after the subject takes in grape juice (Refer to A). On the other hand, the measurements after water intake are similar the previous ones (Refer to B). The graph 801 in FIG. 8A shows that the blood glucose level measuring apparatus 100 according to an embodiment of the present disclosure provides significant results with regard to the blood glucose level.

FIG. 8B shows another graph 802, which compares signals 810 measured with the blood glucose level measuring apparatus 100 according to the present disclosure with signals 820 measured with the invasive blood glucose level measuring apparatus. The intensity of the signals 810 measured with the blood glucose level measuring apparatus 100 according to the present disclosure is higher than that of the signals 820 measured with the invasive blood glucose level measuring apparatus. However, it is observed that characteristic points 821 through 829 among the signals 820 measured with the invasive blood glucose level measuring apparatus are mapped one-to-one onto characteristic points 811 through 819 among the signals 810 measured with the blood glucose level measuring apparatus 100 according to an embodiment of the present disclosure. Therefore, the accurate blood glucose level 820 of the subject are obtained by matching the signals 810 measured with the blood glucose level measuring apparatus 100 according to the present disclosure with the blood glucose level table referred to above.

In this way, the blood glucose level measuring apparatus 100 is capable of providing the subject with accurate information on changes in blood glucose level. In addition, the blood glucose level measuring apparatus 100 is capable of providing the subject with information on the real blood glucose level based on the ratio of the glucose level calculated with the blood glucose level measuring apparatus 100 to the real blood glucose level of the subject.

Figure 9:
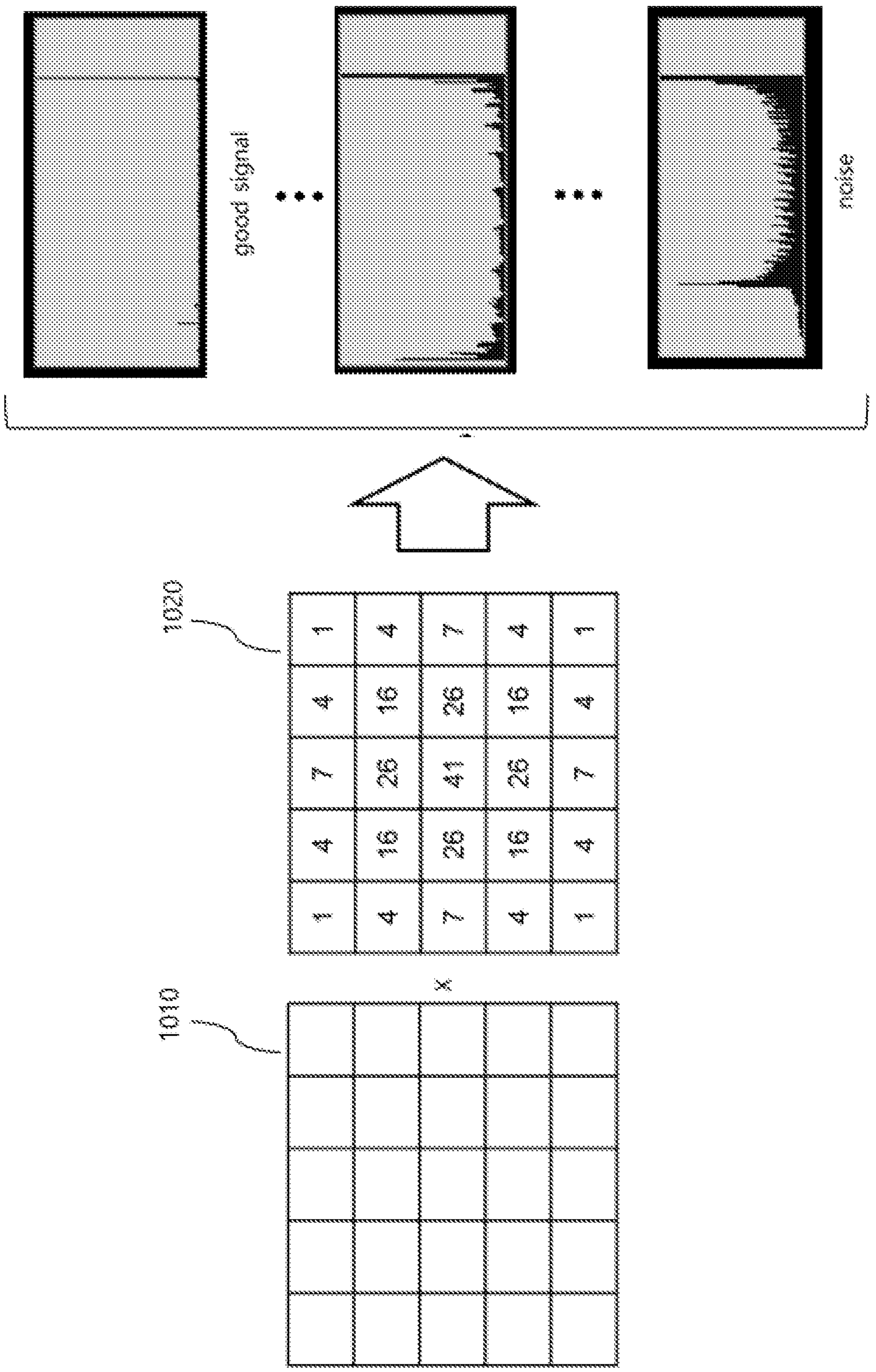
FIG. 9 is an example in which the portable apparatus for noninvasively measuring blood glucose levels according to an embodiment of the present disclosure corrects movement of the subject.

FIG. 9 is an example in which the blood glucose level measuring apparatus according to an embodiment of the present disclosure corrects movement of the subject.

The blood glucose level measuring apparatus 100 could have a form of mobile devices, especially of the wearable devices. Therefore, noise could be generated according to the movement of the subject. Therefore, the photodetecting unit 130 of the blood glucose level measuring apparatus 100 could perform the function of autofocusing.

The photodetecting unit 130 could use the multiple tunneling junction light receiving elements as the detector. For example, as illustrated in FIG. 9, the photodetecting unit 130 could be formed to be a 5×5 array of the tunnel junction light receiving elements.

The photodetecting unit 130 stores the intensity of signals each pixel outputs in the situation where the second LED 120 is switched on. After that, the photodetecting unit 130 is capable of removing or correcting the noise in the output signals on the basis of an autofocusing algorithm and based on the intensity of the stored signals. For example, the photodetecting unit 130 is capable of extracting the noise out of the output signals by applying the Gaussian kernel technique. For example, the noise could be measured with reference to (the intensity of the signal detected at each of the pixels—average of the stored intensities)^2. The photodetecting unit 130 is capable of removing or correcting the signals, among the output signals, which have the noise the intensity of which is equal to or higher than a threshold value and then transmitting the resulting values to the control unit 140.

In the appended Claims, an element described as a means to perform a specific function includes any arbitrary methods to perform the specific function and such an element is capable of including the combination of circuit elements to perform the specific function or software in an arbitrary form which is combined with a suitable circuit to perform software to perform the specific function and includes firmware, microcode and the like.

Referring to the expression of "an embodiment" specified in the present specification and its various derivatives signifies that specific features, structures, characteristics and the like with regard to the embodiment are included in at least one among the embodiments of the principle of the present disclosure. Therefore, the expression of "an embodiment" and arbitrarily selected other modified examples disclosed across the whole of the present disclosure do not refer to an identical embodiment at all times.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

REFERENCE CHARACTERS

100: Portable apparatus for noninvasively measuring blood glucose level
110: First LED
120: Second LED
130: Photodetecting unit
140: Control unit

What is claimed is:

1. A method of operating a portable apparatus for noninvasively measuring blood glucose levels, comprising:

(a) measuring a first signal value by using a photodiode detector when a light source which emits light with a wavelength range to be absorbed into or scattered by glucose is switched off;

(b) measuring a second signal value according to light which is scattered by or transmitted through a tissue of a subject by using the photodiode detector when the light source which emits the light with the wavelength range is switched on;

(c) calculating a glucose concentration measurement of the subject by using the first signal value and the second signal value; and (d) adjusting an intensity of the light emitted from the light source based on the glucose concentration measurement.

2. The method of claim 1, further comprising:

(e) the steps from (b) through (d) are repeatedly performed until the glucose concentration measurement becomes equal to a pre-established first reference value.

3. The method of claim 1, wherein, in the step (d), a driving current for the light source is reduced when a result of subtracting a pre-established first reference value from the glucose concentration measurement is positive, while the driving current for the light source is increased when the result of subtracting the first reference value from the glucose concentration measurement is negative.

4. The method of claim 1, wherein the step (c) comprises:

(c-1) calculating the glucose concentration measurement by correcting the second signal value by subtracting the first signal value from the second signal value; and (c-2) producing blood glucose measuring results of the subject by matching the glucose concentration measurement with a blood glucose level table established to correspond to each glucose concentration.

5. The method of claim 1, the method further comprises:

(f) measuring a third signal value according to the light which is scattered by or transmitted through the tissue of the subject and enters the photodiode detector when a reference light source which emits light with a second wavelength range which are neither absorbed in nor scattered by glucose is switched on;

(g) calculating a compensating value to compensate for a change in an amount of scattering or transmission according to skin characteristics and body temperature of the subject based on a difference between a reference measurement produced by subtracting the first signal value from the third signal value and a second reference value pre-established with reference to a standard subject; and (h) adjusting a driving current for the light source based on the compensating value, prior to the step (b), wherein the wavelength range is 800 to 1000 nm and the second wavelength range 600 to 800 nm.

6. The method of claim 5, wherein the step (b) comprises:

(b-1) measuring the second signal value when the light source driven with a fed back driving current is switched on; and (b-2) measuring again the first signal value when the light source is switched off.

7. The method of claim 5, wherein the step (g) comprises determining the compensating value by comparing the difference between the reference measurement and the second reference value with a table with regard to glucose detection changes according to previously stored skin colors.

8. The method of claim 5, wherein the step (g) comprises reducing the driving current for the light source when the compensating value is positive, and increasing the driving current for the light source when the compensating value is negative.

9. The method of claim 1, the method further comprises (i) removing noise out of and correcting the first signal value and the second signal value based on an autofocusing algorithm.

10. A portable apparatus for noninvasively measuring blood glucose levels, comprising:

a light source which emits light with a wavelength range absorbed into or scattered by glucose;

a photodiode detector which includes at least one light receiving element, for converting light received by the light receiving element to an electrical signal; and a processor which is connected to the photodiode detector and configured to (a) collect a first signal value from the photodiode detector when the light source is switched off, (b) collect a second signal value detected according to the light which is scattered by or transmitted through a tissue of a subject by using the photodiode detector when the light source is switched on, (c) calculate a glucose concentration measurement of the subject by using the first signal value and the second signal value, and (d) adjust an intensity of the light emitted from the light source based on the glucose concentration measurement.

11. The portable apparatus of claim 10, wherein the processor is configured to repeatedly perform (b) through (d) until the glucose concentration measurement becomes equal to a pre-established first reference value.

12. The portable apparatus of claim 10, wherein the processor is configured to reduce a driving current for the light source when a result of subtracting a pre-established first reference value from the glucose concentration measurement is positive, while the driving current for the light source is increased when the result of subtracting the first reference value from the glucose concentration measurement is negative.

13. The portable apparatus of claim 10, wherein the processor is configured to produce the glucose concentration measurement by correcting the second signal value by subtracting the first signal value from the second signal value, and produce blood glucose measuring results of the subject by matching the glucose concentration measurement with a blood glucose level table established to be correspond to each glucose concentration.

14. The portable apparatus of claim 10, the apparatus further comprises a reference light source which emits light with a second wavelength range which are neither absorbed in nor scattered by glucose, wherein the processor is configured to obtain a third signal value detected according to the light which is scattered by or transmitted through the tissue of the subject and enters the photodiode detector by switching the reference light source on when the light source is switched off, calculate a compensating value to compensate for a change in an amount of scattering or transmission according to skin characteristics and body temperature of the subject based on a difference between a reference measurement produced by subtracting the first signal value from the third signal value and a second reference value pre-established with reference to a standard subject and adjust a driving current for the light source based on the compensating value, wherein the wavelength range is 800 to 1000 nm and the second wavelength range 600 to 800 nm.

15. The portable apparatus of claim 14, wherein the second signal value is measured by using the light source driven with the adjusted driving current after switching the reference light source off, and then the first signal value is measured again by switching the light source off.

16. The portable apparatus of claim 14, wherein the processor is configured to determine the compensating value by matching the difference between the reference measurement and the second reference value with the table with regard to glucose detection changes according to previously stored skin colors.

17. The portable apparatus of claim 14, wherein the processor is configured to reduce the driving current for the light source when the compensating value is positive, and increase the driving current for the light source when the compensating value is negative.

18. The portable apparatus of claim 10, wherein the light source and the photodiode detector are arranged on an identical surface so that both of them face an identical surface of the subject or other surfaces opposite to each other so that both of them face each other with the subject in between.

19. A non-transitory computer readable recording medium containing program instructions for achieving a method of operating a portable apparatus for noninvasively measuring blood glucose levels, which when executed by a processor, causes the processor to perform the method, comprising:

(a) collecting a first signal value from a photodiode detector when a light source which emits light with a wavelength range to be absorbed into or scattered by glucose is switched off;

(b) collecting a second signal value according to light which is scattered by or transmitted through a subject tissue by using the photodiode detector when the light source with the wavelength range is switched on;

(c) calculating a glucose concentration measurement of the subject by using the first signal value and the second signal value; and (d) adjusting an intensity of the light emitted from the light source based on the glucose concentration measurement.

20. The portable apparatus of claim 10, wherein the light source is a light emitting diode (LED).

* * * * *